(12) United States Patent
Goto et al.

(10) Patent No.: US 6,812,359 B2
(45) Date of Patent: Nov. 2, 2004

(54) METHOD AND APPARATUS FOR PREPARING FATTY ACID ESTERS

(75) Inventors: Fumisato Goto, Ibaraki (JP); Toshio Sasaki, Ichihara (JP); Katsuyuki Takagi, Sodegaura (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/029,851

(22) Filed: Dec. 31, 2001

(65) Prior Publication Data

US 2003/0065202 A1 Apr. 3, 2003

(30) Foreign Application Priority Data

Sep. 28, 2001 (JP) ........................................ 2001-302900

(51) Int. Cl.[7] .............................................. C07C 51/00
(52) U.S. Cl. ...................................... 554/170; 554/169
(58) Field of Search ................................. 554/169, 170

(56) References Cited

U.S. PATENT DOCUMENTS 4,889,950 A  12/1989 Bott et al.
6,211,390 B1 * 4/2001 Peter et al. .................. 554/170

FOREIGN PATENT DOCUMENTS

| EP | 0985654 A1 | 3/2000 |
| EP | 1061120 A1 | 12/2000 |
| EP | 1061120 * | 12/2000 |
| EP | 1126011 A2 | 8/2001 |
| JP | 2000-109883 A | 4/2000 |
| JP | 2000-143586 A | 5/2000 |

OTHER PUBLICATIONS

Perry' Chemical Engineer's Handbook, McGraw–Hill, 7th ed., pp. 7–20,7–25 to 7–28, 23–45, 1997.*

* cited by examiner

Primary Examiner—Deborah D. Carr
(74) Attorney, Agent, or Firm—Birch, Stewart, Kolasch & Birch, LLP

(57) ABSTRACT

A method for preparing a fatty acid ester with suppressing the discharge of unreacted reactants and/or intermediate products, which comprises reacting fats and oils with a monohydric alcohol in a reactor under conditions where the monohydric alcohol is in a supercritical state, wherein a reaction mixture containing unreacted reactants and/or intermediate products is recycled to the reactor.

6 Claims, 1 Drawing Sheet

METHOD AND APPARATUS FOR PREPARING FATTY ACID ESTERS

BACKGROUND OF THE INVENTION

1. Field of the Invention

The present invention relates to a method and an apparatus for preparing fatty acid esters by reacting fats and oils with a monohydric alcohol.

2. Prior Art

Esters of fatty acids with monohydric alcohols (hereinafter sometimes referred to as "fatty acid esters") are used as industrial raw materials, raw materials in the production of medicaments, fuels, etc. In the field of fuels, they are particularly used as diesel fuels. Furthermore, the fatty acid esters are used as substitute lubricants for conventional mineral oils.

The fatty acid esters are generally prepared by transesterification of fats and oils comprising mainly esters of fatty acids and glycerol, which are called fatty acid triglyceride, with monohydric alcohols.

As a preparation method of fatty acid esters, for example, JP-A 2000-143586 discloses a method comprising reacting methanol with waste soybean oil at 300° C., which is higher than the critical temperature of methanol, under a pressure of 6.5 MPa to obtain fatty acid esters. However, this JP-A publication does not describe the treatment of intermediate products such as diglyceride and unreacted reactants after the reaction.

JP-A 2000-109883 discloses a method for preparing fatty acid esters comprising continuously supplying methanol and a mixture of rapeseed oil and soybean oil in a reactor and reacting them at 270° C., which is higher than the critical temperature of methanol, under a pressure of 12 MPa. However, the yield of the methyl esters of fatty acids is only 60%, and this JP-A publication does not describe the treatment of intermediate products such as diglyceride and unreacted reactants after the reaction either.

When unreacted reactants remain and/or intermediate products form in the conventional methods for preparing fatty acid esters by reacting fats and oils with monohydric alcohols under conditions where the monohydric alcohols are in the supercritical state, the unreacted reactants and/or the intermediate products should be separated from the resulting fatty acid esters and discharged.

SUMMARY OF THE INVENTION

One object of the present invention is to provide a method for preparing a fatty acid ester comprising reacting fats and oils with a monohydric alcohol under conditions where the monohydric alcohol is in a supercritical state, in which the discharge of unreacted reactants and/or intermediate products are suppressed so that the fatty acid ester is obtained in a high yield.

Another object of the present invention is to provide an apparatus suitable for carrying out such a method for preparing a fatty acid ester.

These and other objects of the present invention are achieved by a method for preparing a fatty acid ester comprising reacting fats and oils with a monohydric alcohol in a reactor under conditions where the monohydric alcohol is in a supercritical state, wherein a reaction mixture containing unreacted reactants and/or intermediate products is recycled to the reactor, and an apparatus for preparing a fatty acid ester comprising reacting fats and oils with a monohydric alcohol in a reactor under conditions where the monohydric alcohol is in a supercritical state, wherein the apparatus has a mechanism for recycling a reaction mixture containing unreacted reactants and/or intermediate products to a reactor.

DETAILED DESCRIPTION OF THE INVENTION

Figure 1:
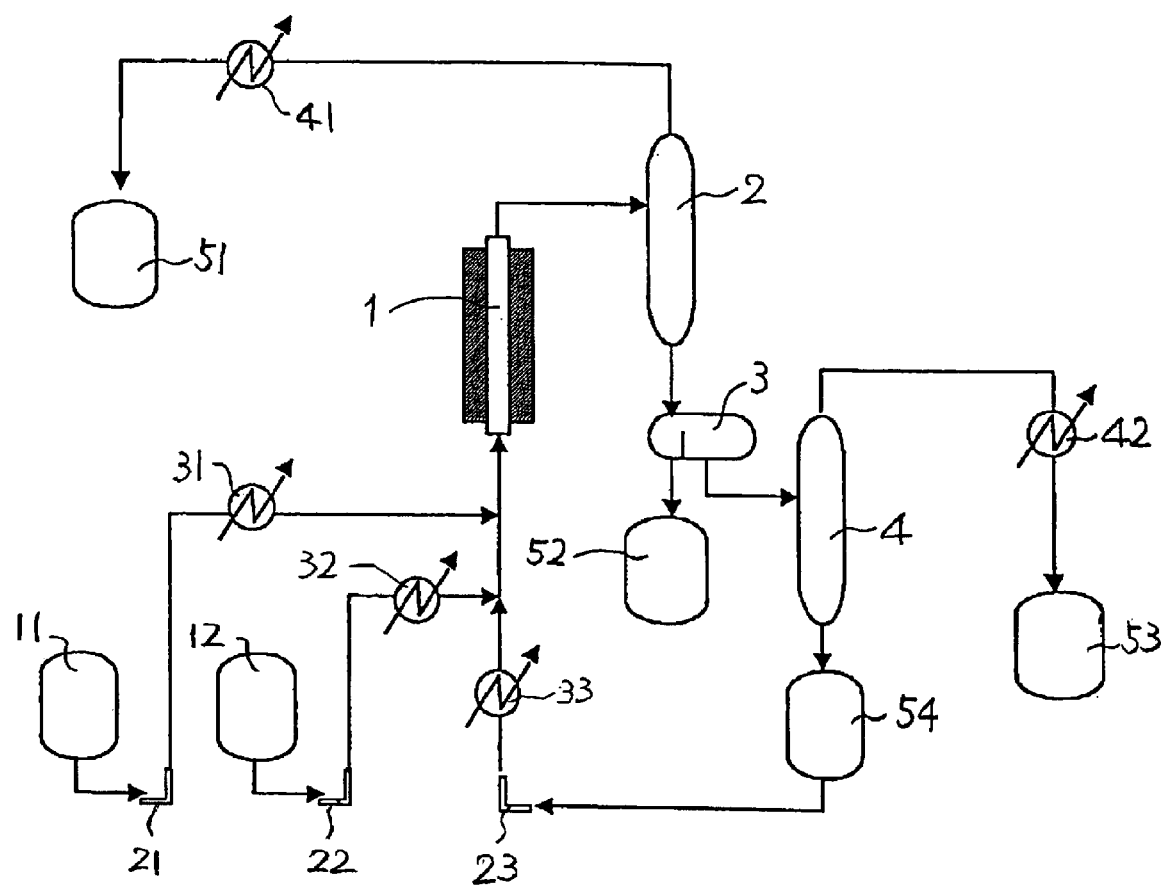
FIG. 1 schematically shows one preferred embodiment of the apparatus for continuously preparing fatty acid esters according to the present invention.

In the method for preparing a fatty acid ester comprising reacting fats and oils with a monohydric alcohol in a reactor under conditions where the monohydric alcohol is in a supercritical state, the reaction mixture obtained through such a reaction contains the unreacted reactants such as fats and oils and/or intermediate products such as diglyceride, monoglyceride, etc.

The prior art methods do not consider the treatment of such unreacted reactants and/or intermediate products contained in the reaction mixture. The present inventors noticed that the unreacted reactants and/or the intermediate products are converted to the final fatty acid ester by recycling the reaction mixture containing the unreacted reactants and/or the intermediate products to the reactor for further reaction, and found that the discharge of the unreacted reactants and/or the intermediate products to outside the reactor can be suppressed, and the yield of the fatty acid ester can be increased. Furthermore, the present inventors found that, when the fatty acid ester is isolated from the reaction mixture containing the unreacted reactants and/or the intermediate products, and a remaining unreacted material liquid is recycled to the reactor, the reaction can further proceed.

The method of the present invention comprises a step of supplying the reaction mixture containing the unreacted reactants and/or the intermediate products to the reactor, and optionally a step of isolating the fatty acid ester from the reaction mixture prior to recycling the reaction mixture to the reactor.

The method of the present invention may be a batchwise method or a continuous method, and the continuous method is preferable.

The fats and oils used in the method of the present invention comprise mainly fatty acid triglyceride, which is an ester of a fatty acid and glycerol. Herein, the "fats and oils comprising mainly fatty acid triglyceride" means that the fats and oils contain at least 50% by weight of the fatty acid triglyceride.

The main reaction in the method according to the present invention is represented by the following reaction scheme:

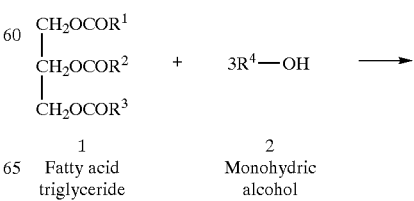

1  Fatty acid triglyceride  2  Monohydric alcohol

-continued

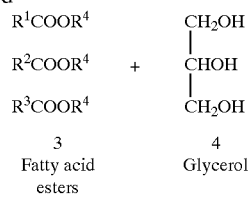

wherein $R^1$, $R^2$ and $R^3$ represent independently each other an hydrocarbon group of a fatty acid, and $R^4$ is a linear or branched hydrocarbyl group which may be substituted with a hydrocarbyloxyl group.

The number of carbon atoms in the $R^1$, $R^2$ and $R^3$ groups depends on the kinds of the fats and oils.

Fats and oils used in the method of the present invention may be natural or synthetic ones.

Specific examples of fats and oils include lard oil, chicken oil, butter oil, beef tallow, cocoa butter oil, corn oil, peanut oil, cottonseed oil, soybean oil, rapeseed oil, coconut butter, olive oil, safflower oil, linseed oil, coconut oil, oak oil, almond oil, apricot kernel oil, oil from seeds of kenaf, beef bone fat, walnut oil, castor oil, chaulmoogra oil, chinese vegetable tallow, cod-liver oil, cotton seed stearin, sesame oil, deer oil, dolphin oil, sardine oil, mackerel oil, horse fat, lard, bone oil, sheep oil, neat's foot oil, palm oil, palm kernel oil, harbor porpoise oil, shark oil, sperm whale oil, tung oil, whale oil, etc. Furthermore, mixtures of two or more fats and oils, fats and oils containing diglyceride and/or monoglyceride, partially modified (e.g. oxidized or reduced) fats and oils, and the like may also be used.

Unpurified fats and oils containing free fatty acids or water or waste edible oils which are discarded from restaurants, food processing factories, homes, etc. maybe used. Preferably, they are pretreated by an appropriate method as needed. For example, when insoluble solids are mixed with the fats and oils before the waste oils such as waste edible oils, etc. are treated by the method of the present invention, they may block a pressurizing pump or a pressure regulating valve and thus interfere with the production of the fatty acid esters. Therefore, the insoluble solids are removed from the fats and oils with a mesh, a filter, etc.

Besides the fatty acid triglyceride, fats and oils may contain other materials. Examples of the other materials include crude oil, heavy oil, gas oil, mineral oil, essential oil, coal, fatty acids, saccharides, metal powders, metal salts, proteins, amino acids, hydrocarbons, flavors, coloring compounds, enzymes, perfumes, alcohols, fibers, resins, rubbers, paints, cements, detergents, aromatic compounds, aliphatic compounds, soot, glass, sand, nitrogen-containing compounds, sulfur-containing compounds, phosphorus-containing compounds, halogen-containing compounds, etc.

It is preferable to remove such other materials by a suitable method such as filtration, distillation, and the like prior to the reaction, when the other materials may interfere with the reaction, or when they are solid materials and block facilities such as pipes used in the production process.

Distillation methods include vacuum distillation, steam distillation, molecular distillation, extractive distillation, etc.

Fats and oils maybe waste fats and oils, waste edible oils, and the like.

The kind of the monohydric alcohol is not limited. Preferably, an alcohol of the formula (1):

R—OH  (1)

wherein R is a hydrocarbyl group having 1 to 10 carbon atoms, or a hydrocarbyloxyl group-substituted hydrocarbyl group having 2 to 10 carbon atoms in total is used.

When the number of the carbon atoms in the hydrocarbyl group R exceeds 10, the fatty acid esters produced by the method of the present invention may not be suitably used as a diesel fuel, which is one of the main applications of the fatty acid esters.

Examples of a hydrocarbyl group having 1 to 10 carbon atoms include alkyl groups, aralkyl groups, alkenyl groups, alkynyl groups, etc.

Specific examples of alcohols of the formula (1) in which R is an alkyl group are methanol, ethanol, n-propanol, isopropanol, n-butanol, isobutanol, sec.-butanol, tert.-butanol, pentanol, hexanol, cyclohexanol, heptanol, etc.

Specific examples of alcohols of the formula (1) in which R is an aralkyl group are benzyl alcohol, α-phenethyl alcohol, β-phenethyl alcohol, etc. Among them, benzyl alcohol is preferable.

Specific examples of alcohols of the formula (1) in which R is an alkenyl group are allyl alcohol, 1-methylallyl alcohol, 2-methylallyl alcohol, 3-buten-1-ol, 3-buten-2-ol, etc. Among them, allyl alcohol is preferable.

Specific examples of alcohols of the formula (1) in which R is an alkynyl group are 2-propyn-1-ol, 2-butyn-1-ol, 3-butyn-1-ol, 3-butyn-2-ol, etc.

Specific examples of alcohols of the formula (1) in which R is a hydrocarbyloxy group-substituted hydrocarbyl group having 2 to 10 carbon atoms in total are 2-methoxyethanol, 2-methoxypropanol, 3-methoxybutanol, etc.

In particular, an alcohol of the formula (1) in which R is an alkyl group having 1 to 4 carbon atoms is preferable. Specific examples of such an alcohol include methanol (R=a methyl group), ethanol (R=an ethyl group), propanol (R=a propyl group), isopropanol (R=an isopropyl group), n-butanol (R=a n-butyl group), isobutanol (R=an isobutyl group) and tert.-butanol (R=a tert.-butyl group). Among them, methanol and ethanol are preferable, and methanol is more preferable.

Alcohols may be used singly or in admixture of two or more alcohols.

The purity of the alcohol is not limited, and is preferably at least 95% by weight, more preferably at least 98% by weight.

Optical isomers of an alcohol may be used, when the alcohol has optical isomers.

The amount of the monohydric alcohol to be supplied is preferably 1 to 100 times, more preferably 2 to 30 times the theoretical supply amount of the monohydric alcohol, which is defined by the following formula:

Theoretical supply amount of monohydric alcohol= (molecular weight of monohydric alcohol)×[{3×(supply amount of fats and oils)/(av. molecular weight of fats and oils)}+{3×(supply amount of unreacted fats and oils)/(av. molecular weight of fats and oils)}+{2×(supply amount of diglyceride)/(av. molecular weight of diglyceride)}+{(supply amount of monoglyceride)/(av. molecular weight of monoglyceride)}]

Here, the average molecular weight of the fats and oils is 56,100×3/(saponification value of fats and oils), the average molecular weight of diglyceride is [(av. molecular weight of fats and oils)×2+92]/3, and the average molecular weight of monoglyceride is [(av. molecular weight of fats and oils)+92×2]/3. The saponification value of fats and oils is an amount (mg) of potassium hydroxide used to completely saponify 1 (one) gram of fats and oils.

When the supply amount of the monohydric alcohol is less than the theoretical supply amount, the yield unpreferably decreases. When the supply amount of the monohydric alcohol exceeds 100 times the theoretical supply amount, the reaction apparatus may become excessively large.

Typical examples of fatty acid esters produced by the method of the present invention include esters of valeric acid, caproic acid, enanthoic acid, caprylic acid, pelargonic acid, capric acid, undecylic acid, lauric acid, tridecylic acid, myristic acid, pentadecylic acid, palmitic acid, heptadecylic acid, stearic acid, nonadecanoic acid, arachidic acid, behenic acid, lignoceric acid, cerotic acid, heptacosanoic acid, montanic acid, melissic acid, lacceric acid, crotonic acid, isocrotonic acid, undecylenic acid, oleic acid, elaidic acid, cetoleic acid, erucic acid, brassidic acid, sorbic acid, linoleic acid, linolenic acid, arachidonic acid, propiolic acid, stearolic acid, nervonic acid, ricinoleic acid, (+)-hydnocarpic acid, (+)-chaulmoogric acid, etc. The kind of an alcohol residue in an ester depends on the kind of the monohydric alcohol used. For example, when methanol is used as an alcohol, a methyl ester is obtained. When ethanol is used as an alcohol, an ethyl ester is obtained.

When fatty acid residues have optical isomers, fatty acid esters include the fatty acid esters of such optical isomers.

In the method of the present invention, the fats and oils are reacted with the monohydric alcohol under conditions where the monohydric alcohol is in the supercritical state.

A supercritical state herein used is now explained.

A material has specific three states, that is, a gas state, a liquid state and a solid state. Furthermore, a material has a fluid state in which it is not condensed by the application of a pressure, when a temperature exceeds a critical temperature. Such a state of a material is a supercritical state.

A fluid in a supercritical state has different properties from those of a liquid or a gas. In a supercritical state, the density of a fluid is close to that of a liquid, the viscosity of a fluid is close to that of a gas, and the thermal conductivity and diffusion coefficient of a fluid are intermediate between those of a gas and a liquid. Thus, the fluid in the supercritical state functions as a non-liquid solvent, and can facilitate a transesterification reaction, although any reason therefor has not been clarified.

In the method of the present invention, the yield of the fatty acid esters may decrease at a temperature at which the monohydric alcohol is not in the supercritical state. When the temperature exceeds 420° C., the fats and oils may be decomposed. A preferred temperature range is from 240° C. to 400° C., more preferably from 245° C. to 350° C.

The temperature condition will be explained more in detail.

When methanol is used as an alcohol, a reaction is carried out at a temperature of at least 240° C., since the critical temperature of methanol is 240° C. When ethanol is used as an alcohol, a reaction is carried out at a temperature of at least 243° C., since the critical temperature of ethanol is 243° C. When n-propanol is used as an alcohol, a reaction is carried out at a temperature of at least 264° C., since the critical temperature of n-propanol is 264° C. When isopropanol is used as an alcohol, a reaction is carried out at a temperature of at least 236° C., since the critical temperature of isopropanol is 236° C. When n-butanol is used as an alcohol, a reaction is carried out at a temperature of at least 287° C., since the critical temperature of n-butanol is 287° C. When tert.-butanol is used as an alcohol, a reaction is carried out at a temperature of at least 233° C., since the critical temperature of tert.-butanol is 233° C. When isobutanol is used as an alcohol, a reaction is carried out at a temperature of at least 275° C., since the critical temperature of isobutanol is 275° C.

The reaction pressure in the method of the present invention is preferably from 0.5 MPa to 25 MPa, more preferably from 2 MPa to 22 MPa, particularly preferably from 8 MPa to 20 MPa. When the pressure is less than 0.5 MPa, the reaction may scarcely proceed. When the pressure exceeds 25 MPa, an apparatus to be used becomes very expensive and thus the method of the present invention may become uneconomical.

In the method of the present invention, the reaction of the fats and oils with the monohydric alcohol is preferably carried out in the absence of a catalyst, since it can proceed in the absence of a catalyst. Alternatively, a catalyst may be used to increase the yield of the fatty acid esters in the case of a single reaction in the batchwise method, or in one path of the reactants through the reactor in the continuous method.

The catalyst to be used in the method of the present invention is not limited. However, alkali catalysts which are soluble in the monohydric alcohol such as sodium hydroxide, lithium hydroxide, potassium hydroxide, etc. may be less preferable, since the separation of such catalysts from the reaction mixture after the reaction is troublesome, and such catalysts may react with the fats and oils to form soaps. Therefore, solid catalysts are preferably used in the method of the present invention.

Examples of the solid catalysts include magnesium oxide, calcium oxide, strontium oxide, barium oxide, lanthanum oxide, calcium hydroxide, strontium hydroxide, sodium carbonate, potassium carbonate, calcium carbonate, magnesium carbonate, barium carbonate, ammonium carbonate, potassium hydrogen carbonate, calcium hydrogen carbonate, sodium ion-exchange zeolite X, potassium ion-exchange zeolite Y, nickel oxides (NiO and $Ni_2O_3$), nickel carbonate, nickel hydroxide, manganese oxide, molybdenum oxide, etc. Among them, sodium carbonate, calcium oxide, calcium hydroxide, calcium carbonate, magnesium oxide, manganese oxide and molybdenum oxide are preferable, since they can achieve a high yield. More preferably, manganese oxide and molybdenum oxide are used. These catalysts may be carried on a solid support such as activated carbon, silica, alumina, zeolite, etc., or mixed or composited with other solid.

The reaction using a catalyst may be carried out in a fixed bed reactor or a suspension bed reactor. In the case of the suspension bed reactor, the amount of the catalyst is preferably from 0.001 to 6 parts by weight, more preferably from 0.01 to 3 parts by weight, based on 100 parts by weight of the fats and oils. If necessary, a means for removing the catalyst may be provided in the downstream of the reactor. The catalyst can be removed by filtration or a method using the difference of weights such as centrifugation.

The method of the present invention can be carried out by a process comprising the following steps (A) to (F). The method of the present invention can be carried out in a batchwise manner or a continuous manner, and the following steps can be applied to the both manners.

(A) a step of supplying fats and oils and a monohydric alcohol in a reactor;

(B) a step of reacting the fats and oils with the monohydric alcohol under conditions where the monohydric alcohol is in the supercritical state to obtain a reaction mixture;

(C) a step of removing the monohydric alcohol from the reaction mixture obtained in step (B) to obtain an alcohol-free reaction mixture;

(D) a step of separating the alcohol-free reaction mixture to a light liquid containing the fatty acid esters and a heavy liquid containing glycerol;

(E) a step of removing the fatty acid esters from the light liquid obtained in step (D) to obtain an unreacted material liquid containing the unreacted reactants and/or intermediate products; and (F) a step of supplying the unreacted material liquid obtained in step (E) to the reactor.

In step (A), the fats and oils and the monohydric alcohol are supplied to the reactor. They may be supplied to the reactor separately, or they may be pre-mixed and then supplied to the reactor. They may be supplied to the reactor continuously or intermittently. Furthermore, the fats and oils and the monohydric alcohol may be preheated with a preheater prior to being supplied to the reactor. In this case, the fats and oils and the monohydric alcohol may be separately supplied to one preheater, or they are mixed and then supplied to the preheater. Alternatively, the fats and oils and the monohydric alcohol may be independently preheated with respective preheaters. In such a case, the preheating conditions in the preheaters may be the same or different. The preheating conditions may be the same as or different from the reaction conditions.

In step (B), the fats and oils and the monohydric alcohol supplied in step (A) and also the unreacted material liquid obtained in step (E) are reacted in the reactor under the conditions where the monohydric alcohol is in the supercritical state to obtain the reaction mixture, When the method of the present invention is carried out in the continuous manner, an average residence time is preferably from 0.5 to 120 minutes, more preferably from 1 to 60 minutes, particularly preferably from 2 to 30 minutes. When the average residence time is less than 0.5 minute, a conversion may be low in some cases. When the average residence time exceeds 120 minutes, the apparatus may become excessively large and thus the method of the present invention may become less economical. Here, the average residence time of the fats and oils and the monohydric alcohol in the reactor is a value obtained by dividing the volume of the reactor by the total volume of the fats and oils and the monohydric alcohol to be supplied in the reactor per a unit time.

The volumes of the fats and oils and the monohydric alcohol are defined as the values calculated using the densities at 25° C. under atmospheric pressure.

When the method of the present invention is carried out in the batchwise manner, a reaction time is usually from 1 to 480 minutes.

In step (C), the monohydric alcohol is removed from the reaction mixture obtained in step (B) to obtain the alcohol-free reaction mixture. In general, the monohydric alcohol is removed by distillation. A pressure in the distillation process is usually atmospheric pressure, or may be elevated or reduced pressure.

In step (D), the alcohol-free reaction mixture obtained in step (C) is separated to the light liquid containing the fatty acid esters and the heavy liquid containing glycerol. The separation is usually carried out by sedimentation using the difference of the specific gravities.

In step (E), the fatty acid esters are removed from the light liquid obtained in step (D) to obtain the unreacted material liquid containing the unreacted reactants and/or intermediate products. The fatty acid esters are usually removed by distillation.

In step (F), the unreacted material liquid obtained in step (E) is supplied (recycled) to the reactor. The unreacted material liquid may be supplied to the reactor independently from the fats and oils and the monohydric alcohol, or it may be mixed with the fats and oils and the monohydric alcohol and then supplied to the reactor. The unreacted material liquid may be supplied to the reactor continuously or intermittently. The unreacted material liquid may be preheated with a preheater prior to being supplied to the reactor. In this case, the unreacted material liquid and the fats and oils or the monohydric alcohol may be separately supplied to one preheater, or they are mixed and then supplied to the preheater. Alternatively, the unreacted material liquid and the fats and oils or the monohydric alcohol may be independently preheated with respective preheaters. In such a case, the preheating conditions in the preheaters may be the same or different. The preheating conditions may be the same as or different from the reaction conditions.

Alternatively, the reaction mixture obtained in step (B) may be firstly separated to a light liquid containing the fatty acid esters and a heavy liquid containing glycerol, and then the monohydric alcohol is removed from the light liquid. In this case, the method of the present invention comprises the following steps:

(A) a step of supplying fats and oils and a monohydric alcohol in a reactor;

(B) a step of reacting the fats and oils with the monohydric alcohol under conditions where the monohydric alcohol is in the supercritical state to obtain a reaction mixture;

(G) a step of separating the reaction mixture obtained in step (B) to a light liquid containing the fatty acid esters and a heavy liquid containing glycerol;

(H) a step of removing the monohydric alcohol from the light liquid obtained in the step (G) to obtain an alcohol-free light liquid;

(I) a step of removing the fatty acid esters from the alcohol-free light liquid obtained in step (H) to obtain an unreacted material liquid containing the unreacted reactants and/or intermediate products; and (J) a step of supplying the unreacted material liquid obtained in step (I) to the reactor.

The purity of the fatty acid esters obtained by the method of the present invention comprising the above steps is preferably at least 95% by weight, more preferably at least 98% by weight. The fatty acid esters obtained are usually mixtures of several esters depending on the structure of the fats and oils used as the raw materials, when natural fats and oils are used. In such a case, the mixtures as such may be used in some applications. Alternatively, a specific fatty acid ester is isolated from the fatty acid ester mixture by a conventional isolation method such as distillation, extraction, etc. and used in some other applications.

In general, the reaction of the fats and oils with the monohydric alcohol takes a long time to complete the reaction, and thus requires a long reactor with a large volume when the reaction is continuously carried out. When the unreacted material liquid is recycled to the reactor in the continuous method, the fatty acid esters can be prepared in a high yield using a short reactor having a relatively small volume even when the conversion is relatively low in one pass of the raw materials through the reactor. If the volume of the reactor is too small or the length of the reactor is too short, the efficiency may decrease. Thus, the reactor is preferably designed so that a yield is from 40 to 90%, preferably from 50 to 80%, in one pass of the raw materials through the reactor.

If necessary, any additional step such as filtration, heating, cooling, transferring, storing, separation, etc. may be included before or after each of the above steps (A) to (J).

The fatty acid esters prepared by the method of the present invention maybe used for a fuel such as a diesel fuel, a lubrication base oil or a fuel additive. In such cases, the fatty acid esters may be used as such or in the form of a mixture with other components depending on requirements of specific applications.

The apparatus of the present invention used to prepare the fatty acid esters will be explained.

The apparatus of the present invention, which is used to prepare the fatty acid esters by reacting the fats and oils with the monohydric alcohol under conditions where the monohydric alcohol is in a supercritical state, has a mechanism for recycling the reaction mixture containing the unreacted reactants and/or the intermediate products to the reactor. Furthermore, the apparatus of the present invention may optionally have a separation means to isolate the fatty acid esters from the reaction mixture containing the unreacted reactants and/or the intermediate products. The apparatus of the present invention may be either a batch type one or a continuous type one. The continuous type apparatus is preferable.

The reaction carried out in the apparatus of the present invention is described above, and the apparatus of the present invention is used to carry out the method of the present invention.

A specific embodiment of the apparatus of the present invention comprises the following components (a) to (f):

(a) a means for supplying fats and oils and a monohydric alcohol in a reactor;

(b) a reactor in which the fats and oils are reacted with the monohydric alcohol under conditions where the monohydric alcohol is in the supercritical state to obtain a reaction mixture;

(c) a separation means for removing the monohydric alcohol from the reaction mixture obtained in the reactor (b) to obtain an alcohol-free reaction mixture;

(d) a separation means for separating the alcohol-free reaction mixture obtained with the separation means (c) to a light liquid containing the fatty acid esters and a heavy liquid containing glycerol;

(e) a separation means for removing the fatty acid esters from the light liquid obtained with the separation means (d) to obtain an unreacted material liquid containing the unreacted reactants and/or intermediate products; and (f) a means for supplying the unreacted material liquid obtained with the separation means (e) to the reactor (b).

The components (a) to (f) of this apparatus are used to carry out steps (A) to (F) of the method of the present invention, respectively.

In another embodiment, the apparatus of the present invention comprises the following components (a), (b) and (g) to (j):

(a) a means for supplying fats and oils and a monohydric alcohol in a reactor;

(b) a reactor in which the fats and oils are reacted with the monohydric alcohol under conditions where the monohydric alcohol is in the supercritical state to obtain a reaction mixture;

(g) a separation means for separating the reaction mixture obtained in the reactor (b) to a light liquid containing the fatty acid esters and a heavy liquid containing glycerol;

(h) a separation means for removing the monohydric alcohol from the light liquid obtained with the separation means (g) to obtain an alcohol-free light liquid;

(i) a separation means for removing the fatty acid esters from the alcohol-free light liquid obtained with the separation means (h) to obtain an unreacted material liquid containing the unreacted reactants and/or intermediate products; and (j) a means for supplying the unreacted material liquid obtained with the separation means (i) to the reactor (b).

The components (a), (b) and (g) to (j) of this apparatus are used to carry out steps (A), (B) and (G) to (J) of the second embodiment of the method of the present invention, respectively.

The continuous type apparatus of the present invention comprising the components (a) to (f) will be explained by making reference to FIG. 1.

The monohydric alcohol and the fats and oils are supplied to the reactor 1 from the tank 11 of the fats and oils and the tank 12 of the alcohol with the pressurizing pumps 21, 22 (means (a)), respectively. The pump may be one having a pressure-resistant structure such as a plunger, etc. When the raw materials are preheated prior to being supplied to the reactor, the preheaters 31, 32 are provided between the respective tanks 11, 12 and the reactor 1. The preheater may be a double-pipe type, a multi-pipe type, a single-pipe type, a block type or a jacket type. Optionally, the preheater may be a plate type or a heat accumulation type (see CHEMICAL EQUIPMENT HANDBOOK, Maruzen (1989) pages 554–564). Furthermore, an electric heating type preheater or an electromagnetic induction heating type preheater may be used. Preferably, the double-pipe type, multi-pipe type or single-pipe type preheater is used.

The raw materials are continuously supplied to the reactor 1 in which the monohydric alcohol is maintained at a temperature at which it is in the supercritical state, while the reaction mixture is continuously discharged from the reactor 1.

The reactor 1 maybe of any type, insofar as it has a structure to maintain the monohydric alcohol at a temperature at which the alcohol is in the supercritical state. Examples of the reactor include a tubular reactor, a vertical or horizontal agitation type reactor, a multi-stage type reactor comprising a plurality of agitation vessels connected in series, an agitation type reactor having baffles, a liquid column gas-injection type reactor, a filling layer type reactor packed with fillings, a plate column type reactor having a plurality of plates, a wetted wall column type reactor, a jetting or spraying type reactor, etc. (see ENCYCLOPEDIA OF CHEMICAL EQUIPMENT (Enlarged Edition) KAGAKUKOGYO Co., Ltd. (1976) pages 399–402). Among them, the tubular reactor is preferable from the economical viewpoint since it can be operated at a high temperature under high pressure. In this case, a perforated plate and the like may optionally be installed in the reactor to prevent the reverse mixing so that the reaction proceeds effectively.

The reaction mixture discharged from the reactor 1 is depressurized with a pressure-regulator (not shown) and then supplied to the alcohol-separation column 2 (separation means (c)) The reaction mixture may optionally be cooled with a cooling means (not shown) prior to being supplied to the column 2.

The unreacted alcohol, which is separated in the alcohol-separation column 2 is condensed with the condenser 41 and then collected in the alcohol-recovering drum 51. The alcohol-free reaction mixture is supplied to the separation drum 3 (separation means (d)) In the separation drum 3, the alcohol-free reaction mixture is separated to a light liquid containing the fatty acid esters and a heavy liquid containing glycerol by gravimetric sedimentation over a sufficient time. The heavy liquid containing glycerol is stored in the tank 52 for glycerol, and may be used as a raw material of industrial glycerol.

The light liquid containing the fatty acid esters is supplied to the distillation column 4 for fatty acid esters (separation means (e)). In the column 4, the fatty acid esters are separated from the light liquid, condensed with the condenser 42 and stored in the tank 53 for the fatty acid esters. The fatty acid esters recovered may be purified with a filter, etc.

The remaining unreacted material liquid containing the unreacted reactants and/or intermediate products is temporarily stored in the tank 54 for the unreacted material liquid, and then supplied (recycled) to the reactor 1 with the pressurizing pump 23 (means (f)). The pump may be the same type one as the pumps 21, 22. The unreacted material liquid may be preheated with the preheater 33 to a temperature higher than the critical temperature of the monohydric alcohol, prior to being supplied to the reactor 1. The preheater 33 may be a double-pipe type, a multi-pipe type or a single-pipe type, which uses steam or a heat transfer medium, or an electric heating type preheater or an electromagnetic induction heating type preheater.

When the method and apparatus of the present invention are used, the discharge of the unreacted raw materials and/or the intermediate products is suppressed, and thus the fatty acid esters can be prepared at a high yield. Even when the reactor having a small volume and a short length is used, the high yield of the fatty acid esters can be achieved.

EXAMPLES

The present invention will be illustrated by the following examples, which do not limit the scope of the invention.

In the Examples, a yield is calculated according to the following formula;

Yield (%)=[{(amount of methyl esters obtained)/296}/{(amount of rapeseed oil supplied)×3/884+(amount of triglyceride supplied)×3/884+(amount of diglyceride supplied)×2/620+(amount of monoglyceride supplied)/356}]×100

Example 1

Rapeseed oil as fats and oils comprising fatty acid triglyceride and methanol as a monohydric alcohol are continuously supplied to respective preheaters at a rate of 187 g/hr. and 540 g/hr., respectively. Simultaneously, as unreacted materials and intermediate products, monoglyceride, diglyceride and triglyceride (besides the rapeseed oil) are continuously supplied to a preheater at a rate of 62 g/hr., 39 g/hr. and 23 g/hr., respectively. All the preheaters are controlled at 200° C. The latter triglyceride is that contained in the rapeseed oil and used as a model compound as an unreacted material.

The amount of methanol supplied is about 17 times the theoretical amount necessary for transesterifying the rapeseed oil, triglyceride, diglyceride and monoglyceride with methanol.

The preheated materials are mixed and continuously supplied to a tubular reactor with an inner diameter of 21 mm having perforated plates provided therein (volume: 260 cc). In this step, the interior of the reactor is adjusted at 250° C. and 12 MPa. The yield was 63%. The average residence time, which is defined above, is 5 minutes.

Thereafter, the reaction mixture is supplied to the alcohol-separation column, and methanol is recovered at a rate of 515 g/hr.

The methanol-free reaction mixture is separated with the separation drum, and glycerol as the heavy liquid is obtained at a rate of 19 g/hr. The mixture from which the heavy liquid is removed is supplied to the distillation column for fatty acid esters. The distilled fatty acid esters are cooled and condensed, and the final fatty acid esters are obtained at a rate of 188 g/hr.

The bottom residue in the distillation column is the unreacted material liquid, which is recycled to the reactor.

Example 2

Rapeseed oil as fats and oils comprising fatty acid triglyceride, methanol as a monohydric alcohol and a 0.5 wt. % slurry of $MnO_2$ powder suspended in methanol are continuously supplied to a preheater at a rate of 187 g/hr., 219 g/hr. and 200 g/hr., respectively. Simultaneously, as unreacted materials and intermediate products, triglyceride, diglyceride and monoglyceride are continuously supplied to respective preheaters at a rate of 9 g/hr., 15 g/hr. and 23 g/hr., respectively. All the preheaters were controlled at 200° C.

The amount of methanol supplied is about 17 times the theoretical amount necessary for transesterifying the rapeseed oil, triglyceride, diglyceride and monoglyceride with methanol.

The preheated materials are mixed and continuously supplied to a tubular reactor with an inner diameter of 21 mm having perforated plates provided therein (volume: 200 cc). In this step, the interior of the reactor is adjusted at 250° C. and 12 MPa. The yield was 82%. The average residence time, which is defined above, is 5 minutes.

The reaction mixture is cooled, and the catalyst is separated and recovered with a centrifugal separator. Thereafter, the reaction mixture is supplied to the alcohol-separation column, and methanol is recovered at a rate of 390 g/hr.

The methanol-free reaction mixture is separated with the separation drum, and glycerol as the heavy liquid is obtained at a rate of 19 g/hr. The mixture from which the heavy liquid is removed is supplied to the distillation column for fatty acid esters. The distilled fatty acid esters are cooled and condensed, and the final fatty acid esters are obtained at a rate of 188 g/hr.

The bottom residue in the distillation column is the unreacted material liquid, which is recycled to the reactor.

What is claimed is:

1. A method for preparing a fatty acid ester comprising reacting fats and oils with a monohydric alcohol under conditions where the monohydric alcohol is in a supercritical state, wherein a reaction mixture containing unreacted reactants and/or intermediate products is recycled to the reactor, and the monohydric alcohol and the fatty acid ester are removed from the reaction mixture prior to being supplied to the reactor.

2. The method according to claim 1, which comprises the steps of:
   (A) supplying fats and oils and a monohydric alcohol in a reactor;
   (B) reacting the fats and oils with the monohydric alcohol under conditions where the monohydric alcohol is in the supercritical state to obtain a reaction mixture;
   (C) removing the monohydric alcohol from the reaction mixture obtained in step (B) to obtain an alcohol-free reaction mixture;
   (D) separating the alcohol-free reaction mixture obtained in step (c) to a light liquid containing the fatty acid esters and a heavy liquid containing glycerol;
   (E) removing the fatty acid esters from the light liquid obtained in step (D) to obtain an unreacted material liquid containing the unreacted reactants and/or intermediate products; and
   (F) supplying the unreacted material liquid obtained in step (E) to the reactor.

3. The method according to claim 1, which comprises the steps of:
   (A) supplying fats and oils and a monohydric alcohol in a reactor;
   (B) reacting the fats and oils with the monohydric alcohol under conditions where the monohydric alcohol is in the supercritical state to obtain a reaction mixture;

(G) separating the reaction mixture obtained in step (B) to a light liquid containing the fatty acid esters and a heavy liquid containing glycerol;

(H) removing the monohydric alcohol from the light liquid obtained in the step (G) to obtain an alcohol-free light liquid;

(I) removing the fatty acid esters from the alcohol-free light liquid obtained in step (H) to obtain an unreacted material liquid containing the unreacted reactants and/or intermediate products; and (J) supplying the unreacted material liquid obtained in step (I) to the reactor.

4. The method according to any one of claims 1, 2 and 3, wherein said monohydric alcohol is an alcohol of the formula:

$$R-OH$$

wherein R is a hydrocarbyl group having 1 to 10 carbon atoms, or a hydrocarbyloxyl group-substituted hydrocarbyl group having 2 to 10 carbon atoms in total.

5. The method according to claim 1, which further comprises a step of preheating with at least one preheater, the fats, oils and monohydric alcohol either separately or in combination prior to being supplied to the reactor.

6. The method according to claim 1, wherein step (A) further comprises supplying a catalyst to the reactor.

* * * * *